(12) United States Patent
Feenstra et al.

(10) Patent No.: US 7,186,741 B2
(45) Date of Patent: Mar. 6, 2007

(54) NEUROTENSIN ACTIVE 2,3,DIARYL-PYRAZOLIDINE DERIVATIVES

(75) Inventors: Roelof W. Feenstra, Weesp (NL); Josephus H. M. Lange, Weesp (NL); Maria L. Pras-Raves, Weesp (NL); Cornelis G. Kruse, Weesp (NL); Herman H. van Stuivenberg, Weesp (NL); Tinka Tuinstra, Weesp (NL); Hiskias Keizer, Weesp (NL)

(73) Assignee: Solvay Pharmaceuticals B.V., Weesp (NL)

(*) Notice: Subject to any disclaimer, the term of this patent is extended or adjusted under 35 U.S.C. 154(b) by 450 days.

(21) Appl. No.: 10/490,549

(22) PCT Filed: Mar. 17, 2003

(86) PCT No.: PCT/EP03/50064

§ 371 (c)(1),
(2), (4) Date: Mar. 23, 2004

(87) PCT Pub. No.: WO03/078400

PCT Pub. Date: Sep. 25, 2003

(65) Prior Publication Data

US 2004/0242493 A1   Dec. 2, 2004

(30) Foreign Application Priority Data

Mar. 18, 2002   (EP) .................... 02076482

(51) Int. Cl.
*A61K 31/415* (2006.01)
*C07D 231/04* (2006.01)
*C07D 401/04* (2006.01)

(52) U.S. Cl. ............... 514/406; 548/356.1; 548/364.1; 546/268.1; 546/275.4; 514/403

(58) Field of Classification Search ............ 548/356.1, 548/364.1; 514/403, 406; 546/268.1, 275.4
See application file for complete search history.

(56) References Cited

U.S. PATENT DOCUMENTS 4,912,127 A    3/1990   Henning et al.
5,502,059 A *  3/1996   Labeeuw et al. ........... 514/296
5,585,497 A * 12/1996   Labeeuw et al. ......... 548/374.1

FOREIGN PATENT DOCUMENTS

EP    0 647 629 A1    4/1995

* cited by examiner

*Primary Examiner*—Golam M. M. Shameem
(74) *Attorney, Agent, or Firm*—Finnegan, Henderson, Farabow, Garrett & Dunner, L.L.P.

(57) ABSTRACT

The invention relates to a group of novel 2,3 diaryl-pyparazolidine derivatives having formula (1). The symbols used in formula (1) have the meanings given in the specification. The compounds have inhibiting activity on enzymes which degrade the neuropeptide neurotensin and can be used for the treatment of affections and diseases caused by disturbances of the neurotensin mediated transmission.

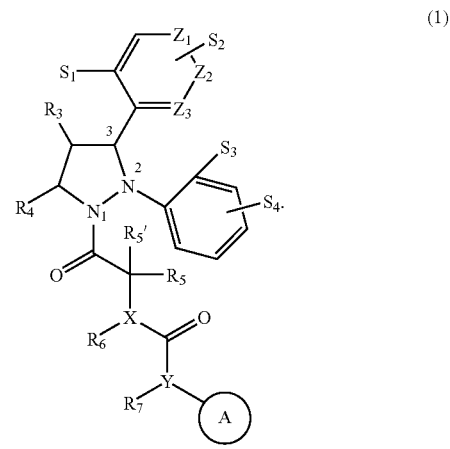

4 Claims, 6 Drawing Sheets

NEUROTENSIN ACTIVE 2,3,DIARYL-PYRAZOLIDINE DERIVATIVES

The invention relates to a group of new 2,3-diaryl-pyrazolidine derivatives having inhibiting activity on enzymes which degrade the neuropeptide neurotensin.

It has been found that compounds having formula (1)

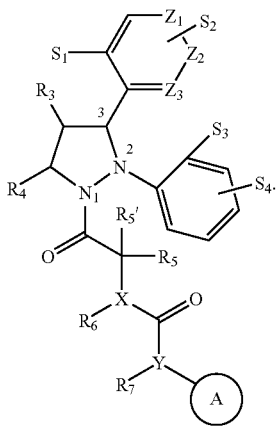

wherein,

- $S_1$ is hydrogen, halogen, hydroxy or alkoxy (1–3C)
- $S_2$ is hydrogen or halogen
- $S_3$ is hydrogen, halogen, hydroxy or alkoxy (1–3C)
- $S_4$ is hydrogen, halogen or alkyl (1–6C) optionally substituted with hydroxy, alkoxy (1–3C), amino, mono- or dialkylamino having 1–3C-atoms in the alkyl group(s), SH or S-alkyl (1–3C)
- X represents nitrogen or carbon
- Y represents nitrogen or oxygen when X is nitrogen, or Y is nitrogen when X is carbon
- $R_3$ and $R_4$ are independently of each other hydrogen or alkyl (1–3C)
- $R_5$ is hydrogen or alkyl (1–6C) which may be substituted with halogen, CN, $CF_3$, hydroxy, alkoxy (1–3C), sulfonylalkyl (1–3C), amino, mono- or dialkylamino having 1–3C-atoms in the alkyl group(s) when X is carbon or nitrogen, or $R_5$ represents alkoxy (1–6C), SH or S-alkyl (1–3C) when X is carbon
- $R'_5$ is hydrogen or alkyl (1–3C)
- $R_6$ is hydrogen, or alkyl (1–3C)
- $R_7$ is hydrogen or alkyl (1–3C)
- $R_5$ and $R_6$ together or $R'_5$ and $R_6$ together can form a 3–7 membered cyclic group which may be substituted with lower alkyl, halogen, CN or $CF_3$, and $R_5+R'_5$ together may form a 3–7 membered ring, and
- $Z_1$, $Z_2$ and $Z_3$ represent carbon, or $Z_1$ is nitrogen and $Z_2$ and $Z_3$ are carbon, or $Z_1$ and $Z_3$ are carbon and $Z_2$ is nitrogen, or $Z_1$ and $Z_2$ are carbon and $Z_3$ is nitrogen,
- A is a (poly) cycloalkyl system consisting of 4–10 membered rings which can be substituted with halogen, $CF_3$, alkyl or alkoxy (1–3C), CN, OH or SH and salts thereof have neurotensin degrading enzyme inhibiting activity.

More particularly the compounds inhibit the enzymes Thimet oligopeptidase EC 3.4.24.15 and Neurolysine EC 3.4.24.16 which break down the neuropeptide neurotensin.

Due to the inhibition of the neurotensin degrading activity of these enzymes the levels of endogenous neurotensin will rise, causing benificial effects in the treatment of diseases in which neurotensin levels are disturbed.

The compounds according to the invention are active in inhibiting the abovementioned enzymes in the range of 5.0–8.0 ($pIC_{50}$ values), when tested according to the methods described in Biochem. J. 280, 421–426, and Eur. J. Biochem. 202, 269–276.

The compounds according to the invention can be used for the treatment of affections and diseases caused by disturbances of the neurotensin mediated transmission, such as peripheral disturbances like regulation of blood pressure and gastric emptying, neurological disturbances like Parkinson's disease, and central nervous system (CNS) disturbances like anxiety, depression, psychosis and other psychosis disorders.

Figure 1:
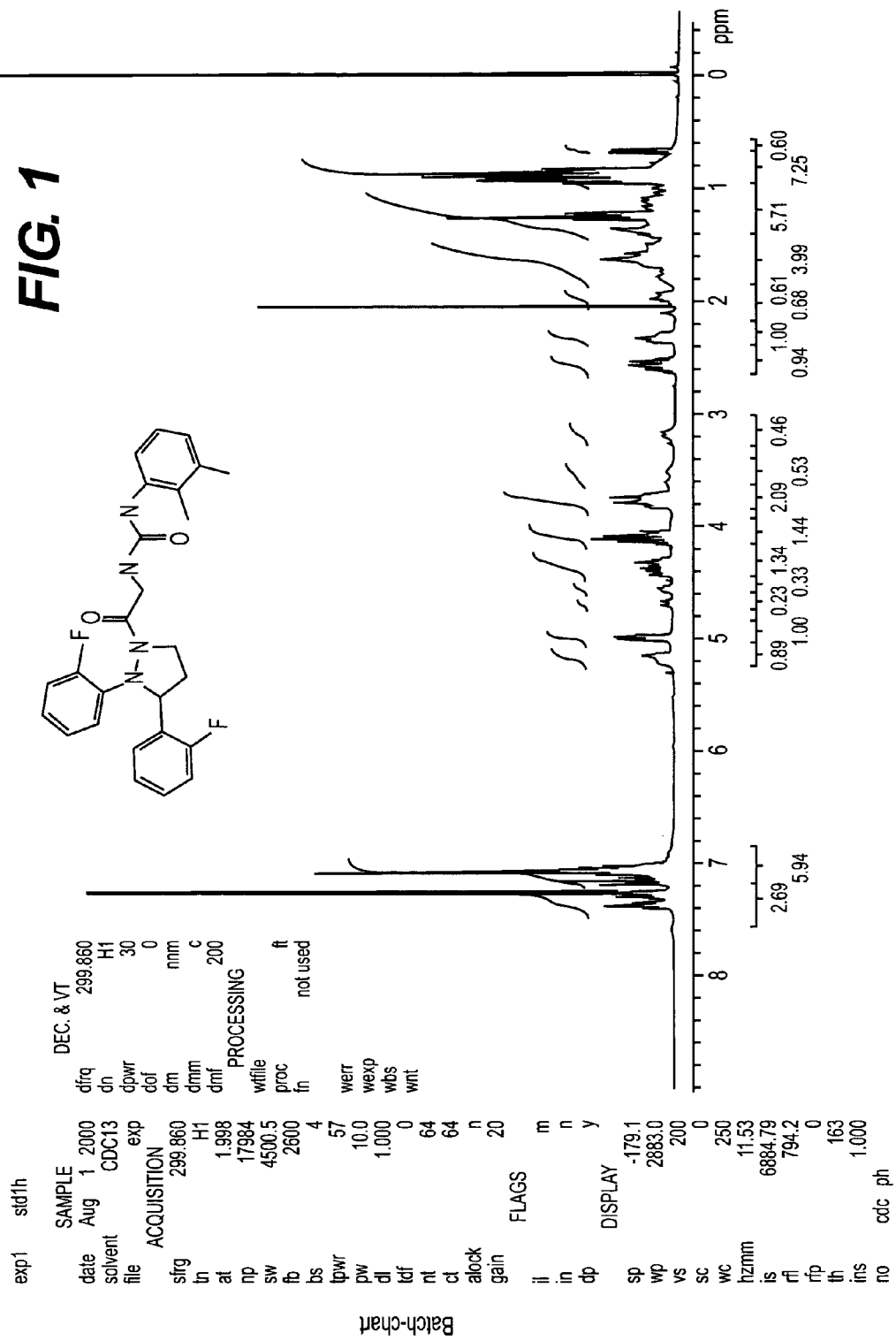
FIG. 1 depicts an NMR spectra for compound A1.
Figure 2:
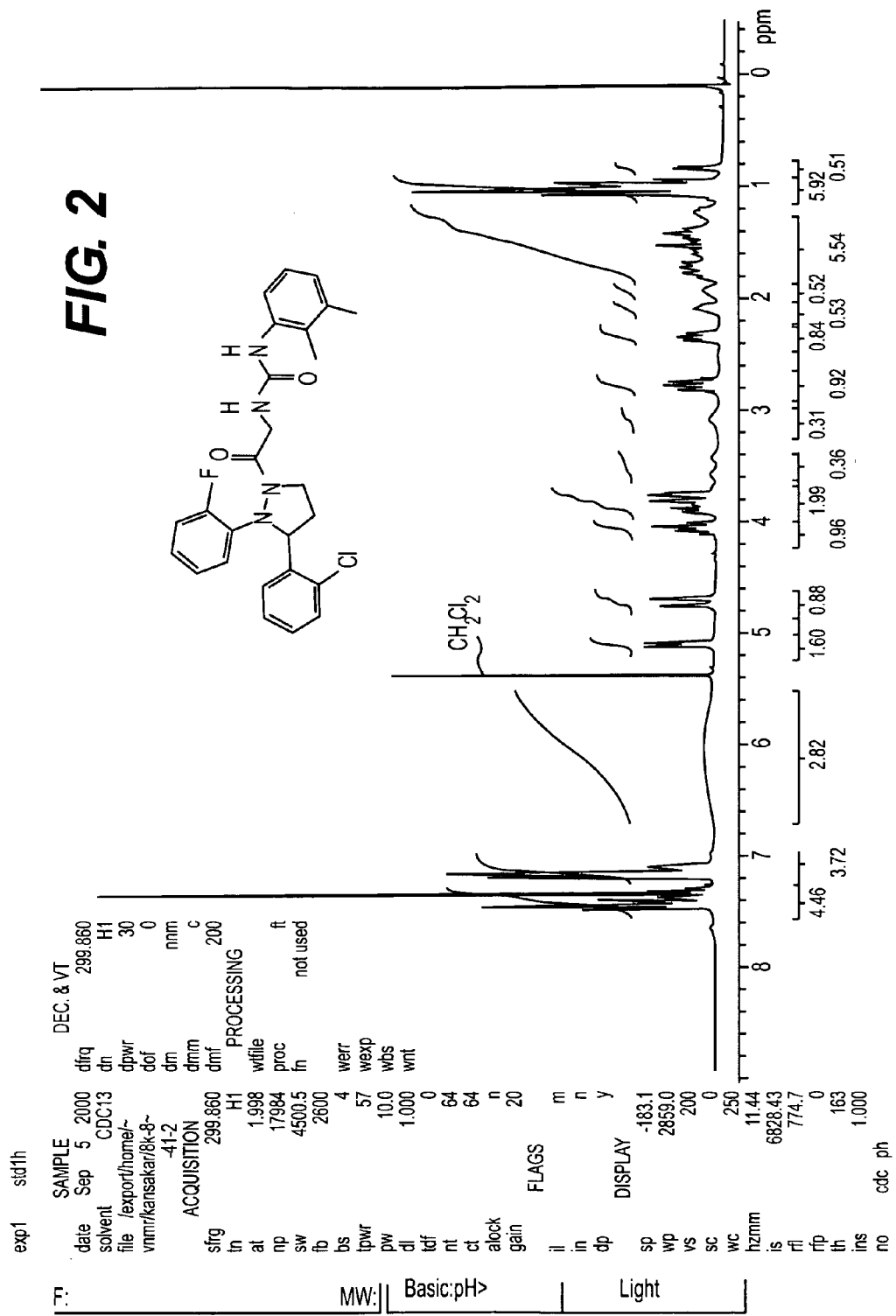
FIG. 2 depicts an NMR spectra for compound A2.
Figure 3:
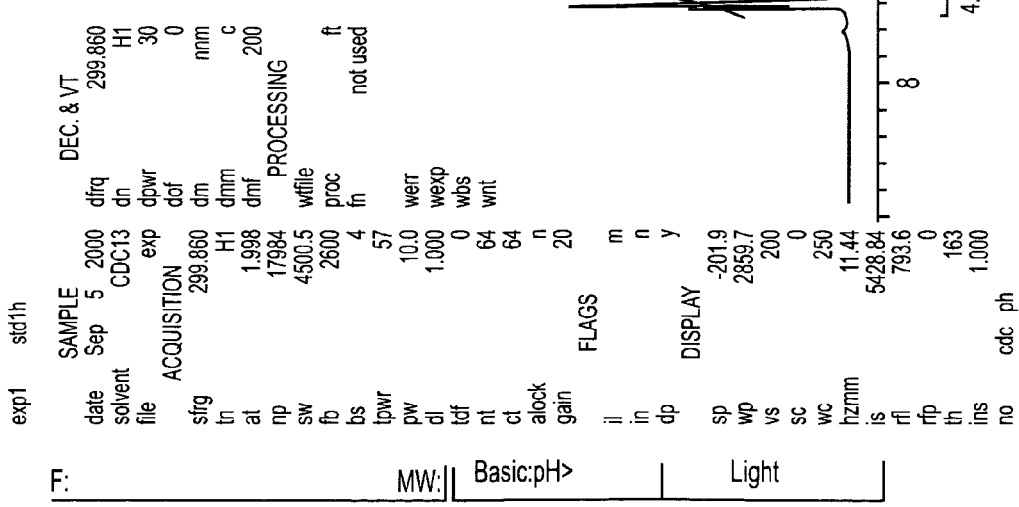
FIG. 3 depicts an NMR spectra for compound A3.
Figure 4:
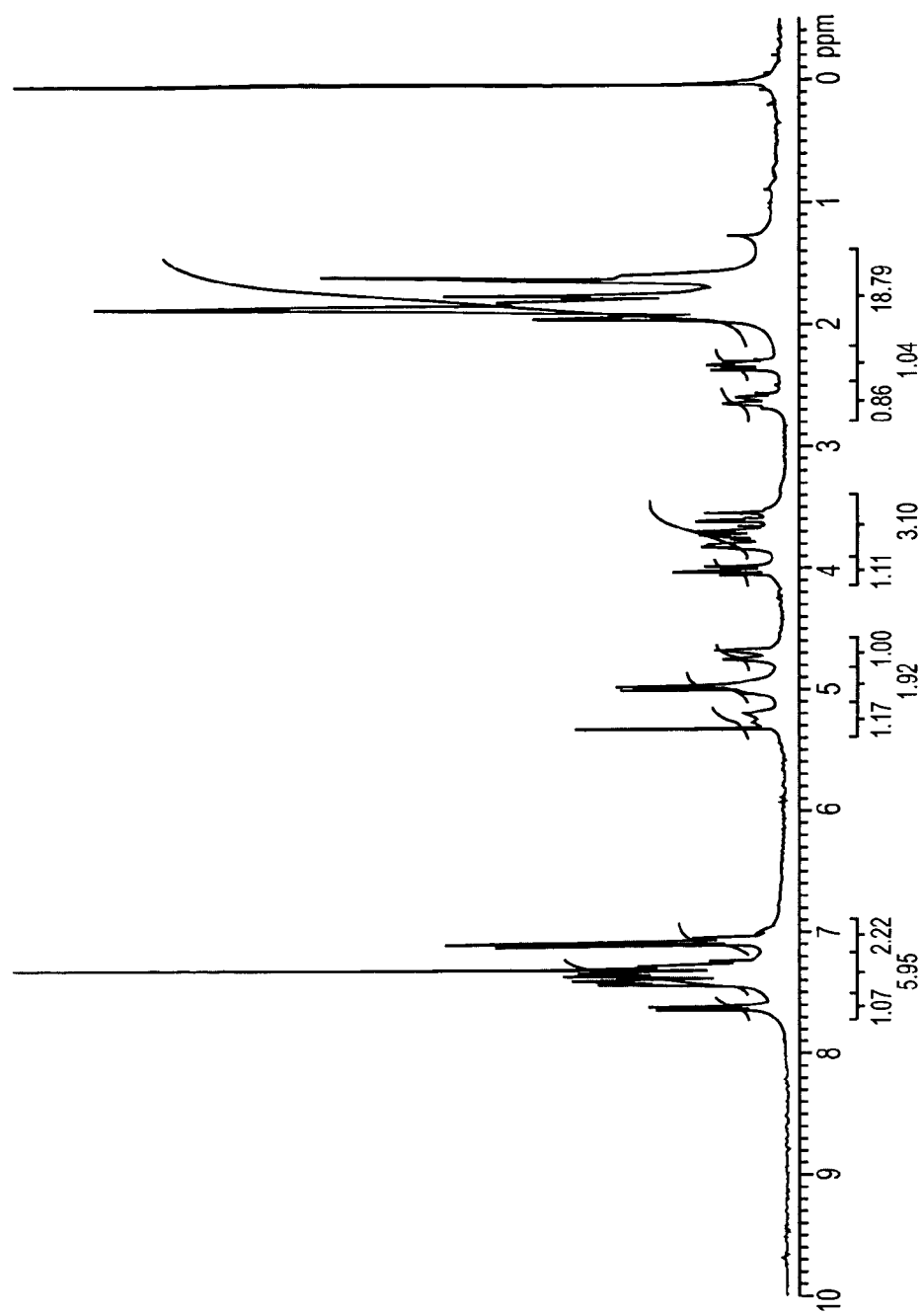
FIG. 4 depicts an NMR spectra for compound A18.
Figure 5:
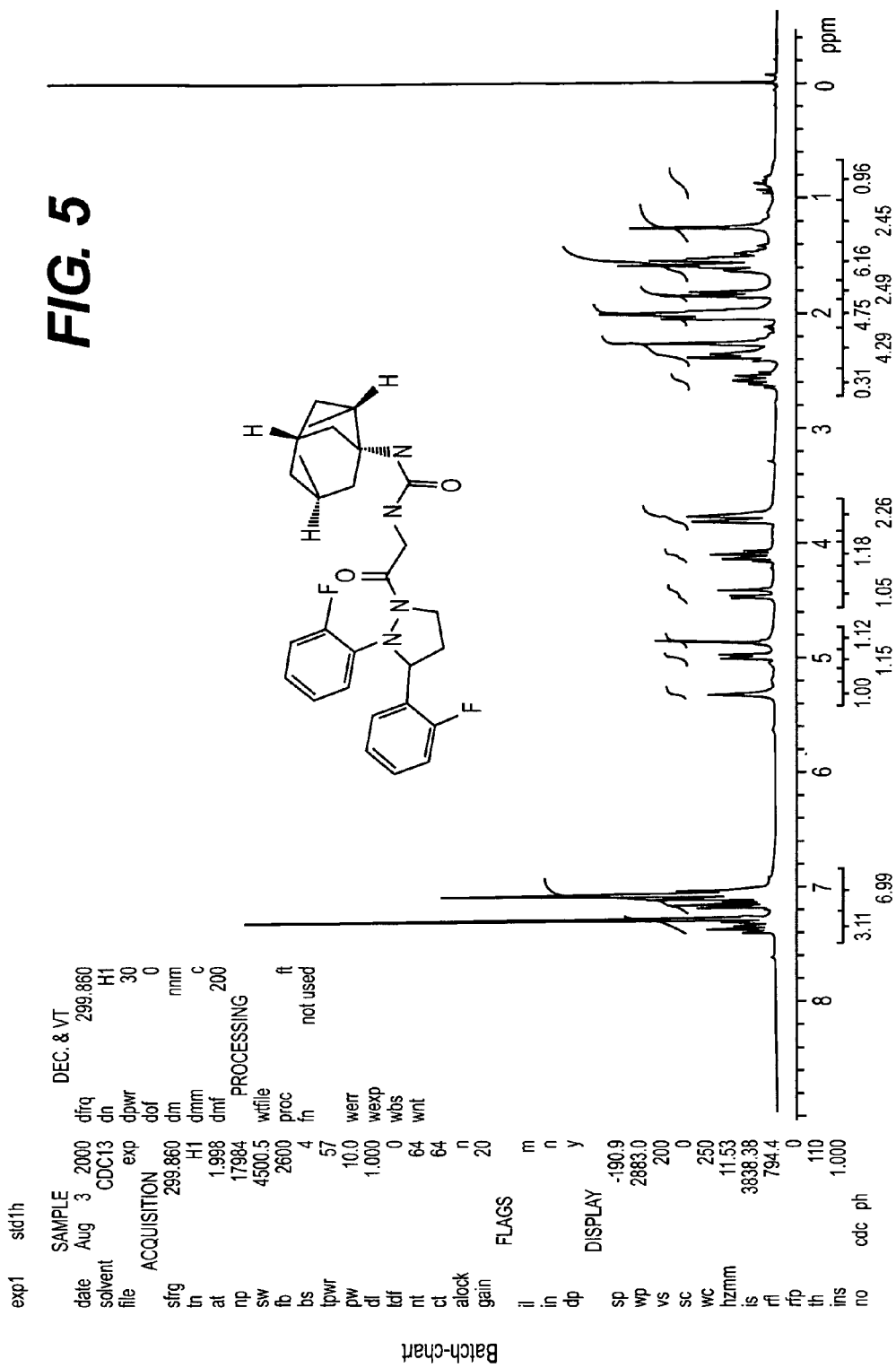
FIG. 5 depicts an NMR spectra for compound A22.
Figure 6:
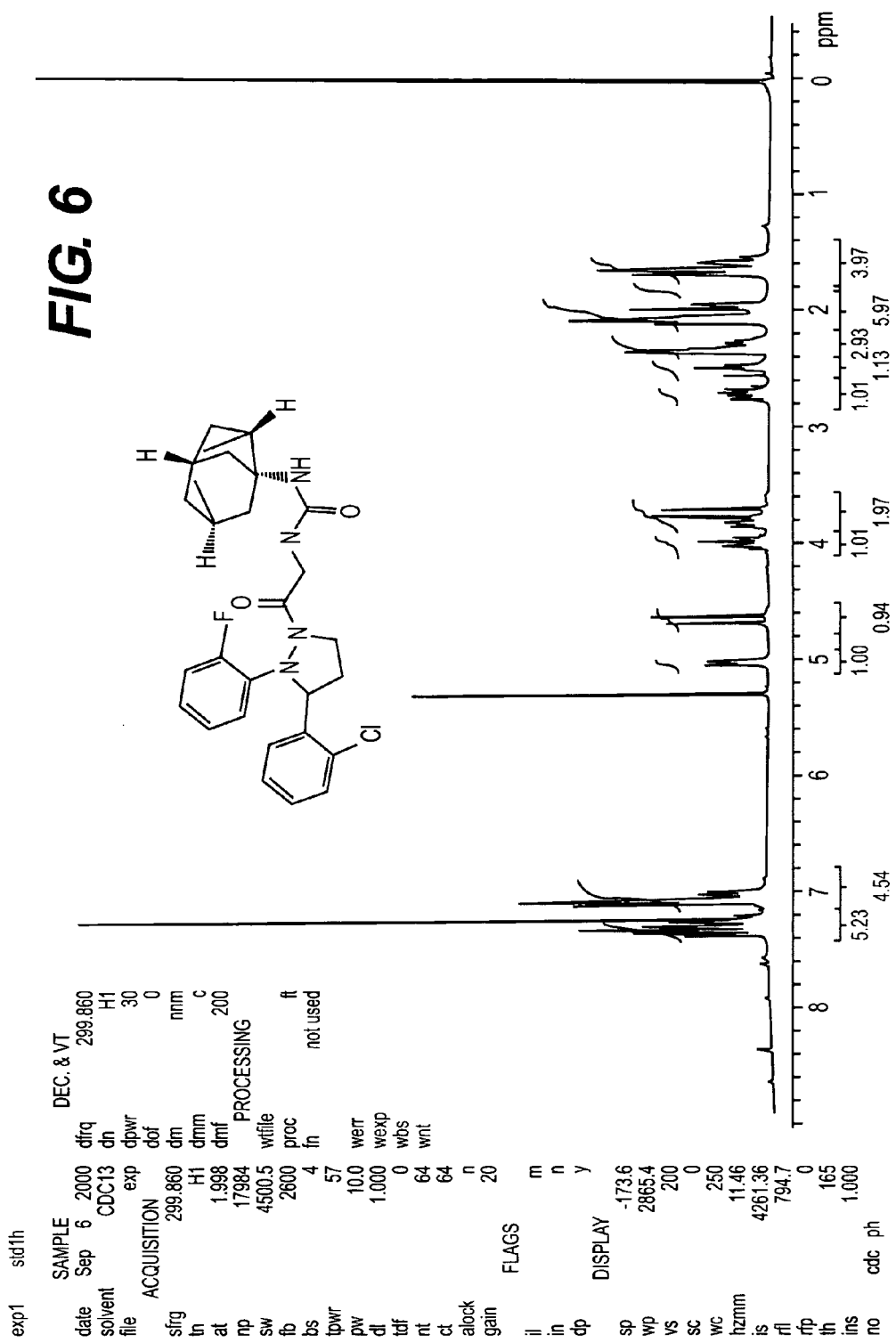
FIG. 6 depicts an NMR spectra for compound A29.

The compounds having the formula (1) can be obtained according to at least one of the following four methods A, B, C and D. The starting compounds for these four methods are substituted 2,3-diaryl-pyrazolidines having one of the structures indicated in Illustration 1:

Illustration 1

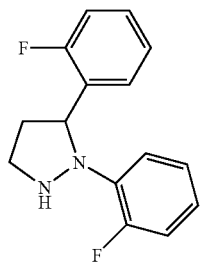

I

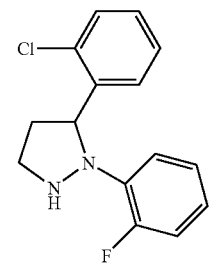

II

-continued
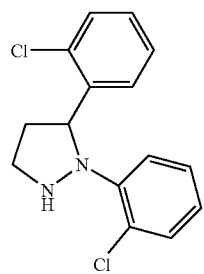
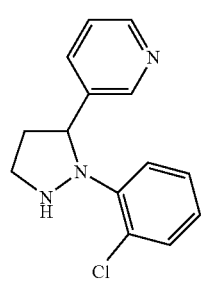
The part R$_7$—Y—A of the compounds having formula (1) can have the structures of the groups indicated in Illustration 2:

-continued

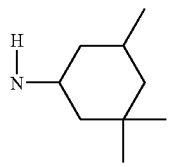

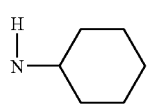

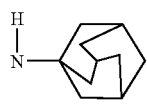

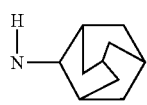

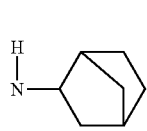

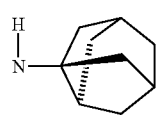

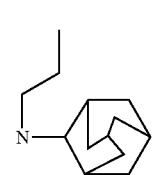

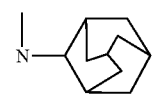

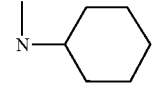

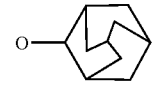

-continued

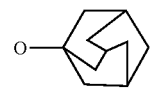

The starting pyrazolidine derivatives of Illustration 1 can be obtained according to the method of Scheme 1:

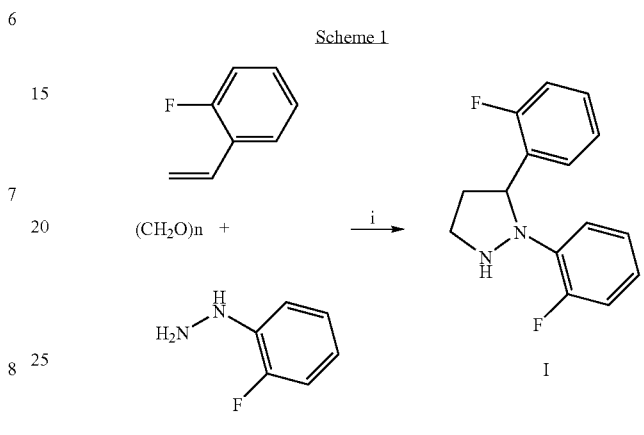

as elucidated in Example 5

Method A:

The compounds mentioned the compounds mentioned in table A, can be synthesized according to the synthesis of compound A23/A24. After step i two diastereomers evolve which, after step iii has been performed, can be separated by column chromatography into enantiomeric pure diastereomers A23 and A24. See scheme A.1.

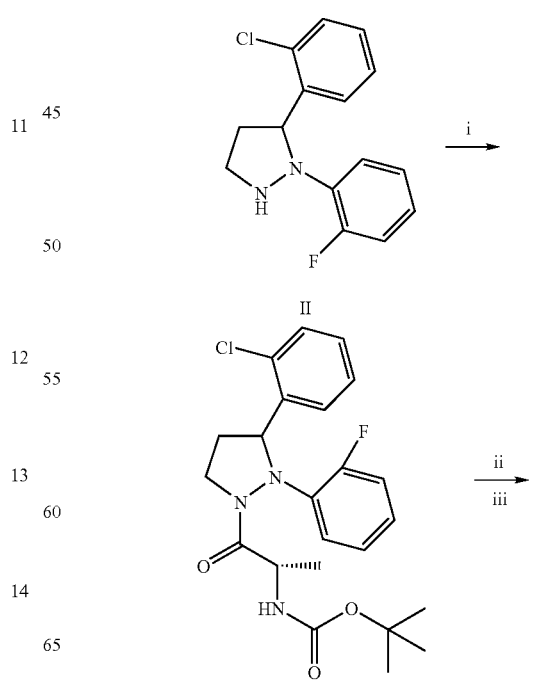

7

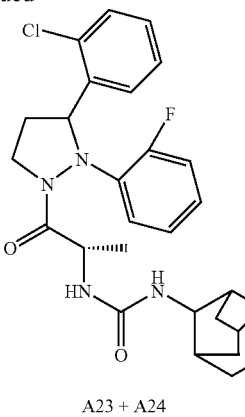

A23 + A24

Method B:

The compounds mentioned in Table B can be obtained according to the synthesis indicated in Scheme B.1.

Scheme B.1

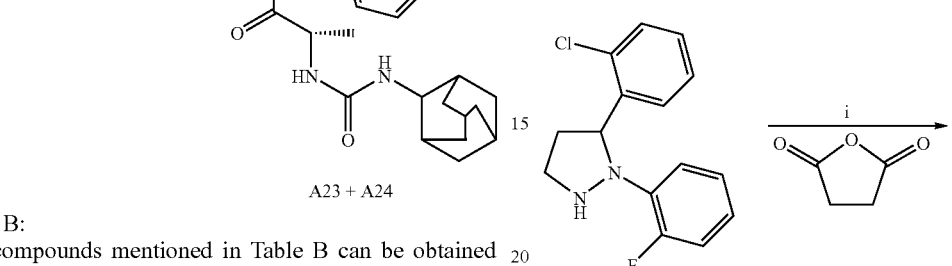

8

Reaction step i and ii of Scheme B.1 are indentical to the procedures described in Scheme A.1, step i and step ii respectively.

Method C:

The compounds mentioned in Table C can be prepared according to the synthesis of compounds C2 and C8 as depicted in Scheme C.1:

Scheme C.1

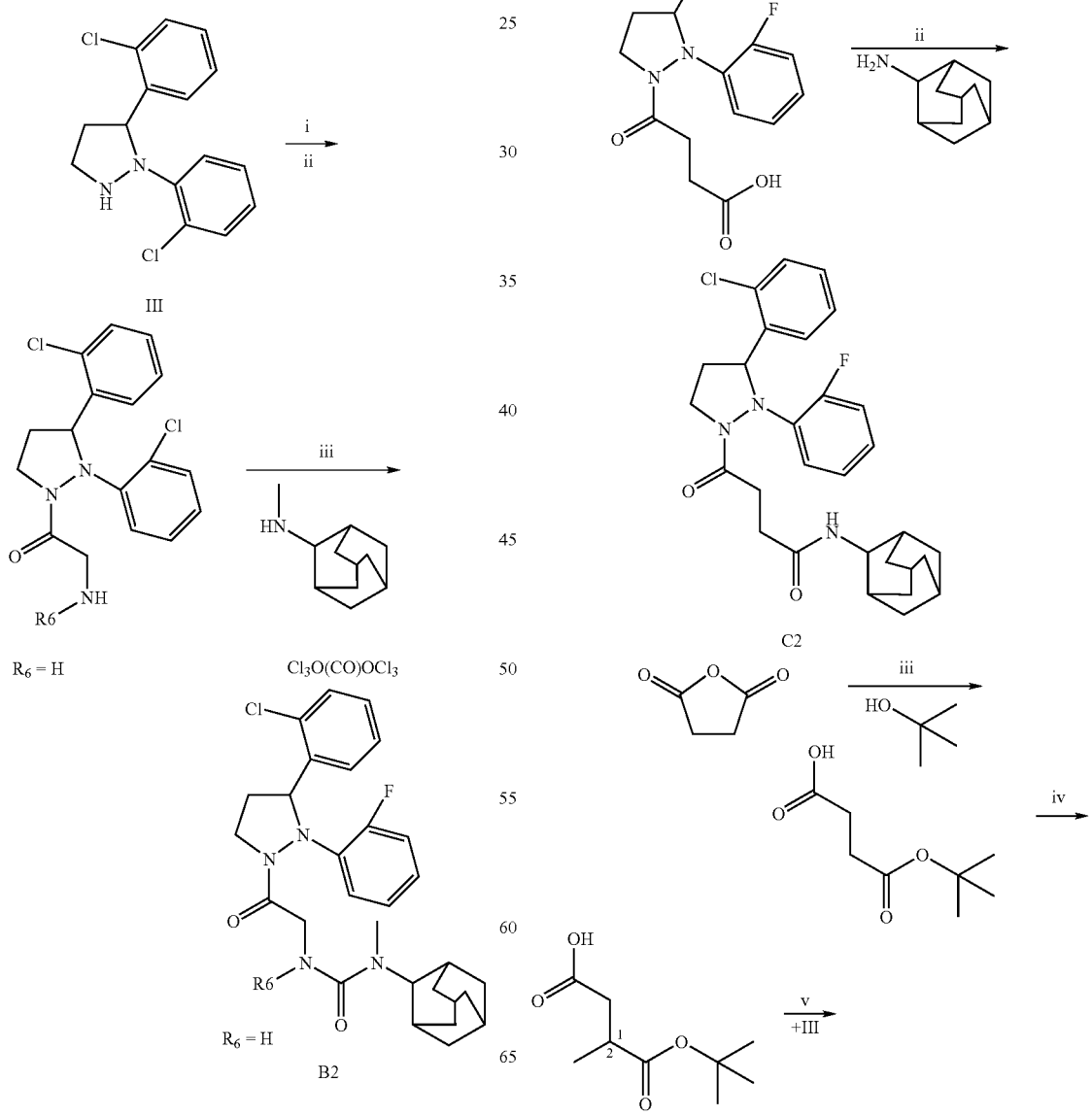

-continued

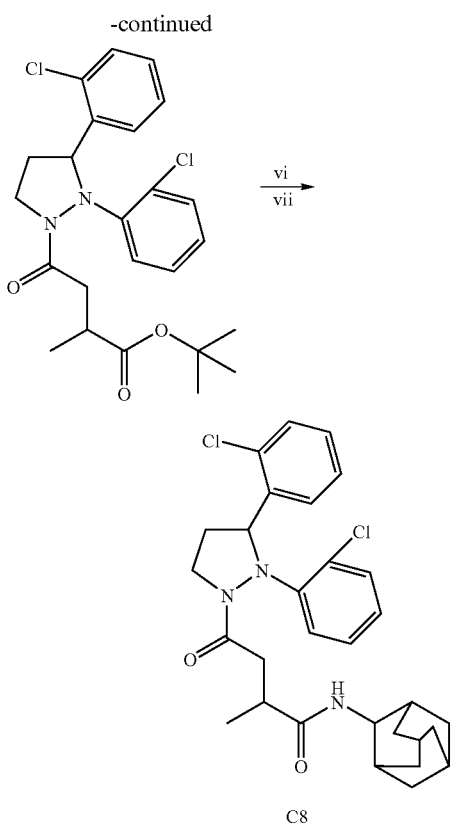

C8

Method D:

The compounds mentioned in Table D can be obtained according to the synthesis of compound D1 as indicated in Scheme D.1:

Reaction step i and ii of Scheme D.1 are identical to the procedures described in Scheme C.1 reaction steps iii and iv respectively.

The preparation of the compounds having formule (1) and of a number of intermediates according to methods A–D will now be described in detail in the following Examples.

EXAMPLE 1

Step i (Scheme A.1):

To a stirred 50 ml of dry acetonitril at room temperature and under a nitrogen atmosphere, were added: 4 g (14.5 mmol) of II, 2.7 g (14.3 mmol) of N-Boc-L-Alanine and 3.8 g (18.4 mmol) of DCC (dicyclohexylcarbodiimide). A precipitate formed directly. Stirring was continued for one night. Thin layer chromatography of the reaction mixture displays a 8-like double spot containing the two possible diastereomers. The precipitate was removed by filtration. To the filtrate about 20 g of silica was added and concentrated in vacuo. The resulting powder was put on top of a dry column (SiO$_2$) after which elution was performed (eluent: CH$_2$Cl$_2$/MeOH 98/2). The part of the column containing the two diastereomers was collected and taken into MeOH. The latter suspension was filtered, the residu washed one more time with MeOH. The combined MeOH fractions were concentrated in vacuo and the resulting residu taken into CH$_2$Cl$_2$ after which it was dried on MgSO$_4$. Removal of the drying agent by filtration and solvent by evaporation in vacuo, ca. 5 g (80%) of crude product was isolated.

Step ii (Scheme A.1):

While stirring, the 5 g (ca. 10 mmol) resulting from step i, were dissolved in 100 ml of a solution consisting of trifluoroacetic acid/CH$_2$Cl$_2$/H$_2$O 70/25/5. Stirring was continued for 2 hours. Subsequently the reaction mixture was concentrated in vacuo, the resulting residu was taken into CH$_2$Cl$_2$. The latter solution was treated with a saturated K$_2$CO$_3$ (aq) solution, and washed with water and brine and eventually dried on MgSO$_4$.

After removal of the drying agent by filtration and the solvent by evapotation in vacuo, 4 g (ca. 100%) of the crude amine was isolated.

Step iii (Scheme A.1):

At room temperature and under a nitrogen atmosphere, 0.50 g (1.44 mmol) of the crude amine of step ii was suspended in 10 ml of acetonitril while stirring. Subsequently, 0.26 g (1.44 mmol) of 2-adamantylisocyanate was added. The reaction was continued for 2 hours. To the reaction mixture about 2 g of silica was added and concentrated in vacuo. The resulting powder was put on top of a dry column (SiO$_2$) after which elution was performed (eluent: EtOAc/petroleum ether 1/1). The parts of the column containing the diastereomers were collected separately, and taken into MeOH. The resulting two suspensions were separately filtered, each of the the two residues washed with MeOH one time. For each diastereomer the corresponding MeOH fractions were combined and concentrated in vacuo after which each residue was taken into CH$_2$Cl$_2$ after which the two solutions were dried on MgSO$_4$. After removal of the drying agent and the solvent in vacuo, two solids, each containing one diastereomer, were obtained: 0.16 g of A23 (21%), melting point 140–3° C., and 0.22 g of A24 (29%) melting point 145–8° C.

Note:

Compound A12 has been prepared enantiomerically pure. The intermediate after step ii (scheme A.1), was separated into its enantiomers after which step iii (scheme A.2) was performed. The (+)-enantiomer of A12 was the eutomer.

The separation into the enantiomers of the intermediate after step ii (scheme A.1) was accomplished by using a Chiralcel CD column (25×5 cm$^2$, 20μ, eluent: hexane/ethanol 4/1).

The compounds of Table A have been prepared in the same manner:

TABLE A

R$_3$, R$_4$, R$_6$, R$_7$, S$_2$, S$_4$ = H
X, Y = N

| Compound | pyrazolidine | R$_5$ | R$_5$' | YR$_7$A | remark | melting point |
|---|---|---|---|---|---|---|
| A1 | I | H | H | 1 | | see app. 1 |
| A2 | II | H | H | 1 | | see app. 2 |
| A3 | II | H | H | 2 | | see app. 3 |
| A4 | III | H | H | 3 | | 153–5 |
| A5 | III | H | H | 4 | | >220 |
| A6 | II | H | H | 5 | | 185–8 |
| A7 | II | H | H | 4 | | 120–5 |
| A8 | II | H | H | 6 | | 130–3 |
| A9 | III | H | H | 6 | | 195–8 |
| A10 | IV | H | H | 7 | | 241–2 |
| A11 | III | H | H | 7 | | >280 |
| A12 | III | H | H | 8 | [α] +94 | 164–5 |
| A13 | II | H | H | 8 | | 135–40 |
| A14 | II | H | H | 9 | | 105–10 |
| A15 | III | H | H | 8 | | 168–71 |
| A16 | I | H | H | 7 | | 208–210 |
| A17 | II | H | H | 7 | | 115–120 |
| A18 | V | H | H | 7 | | see app. 4 |
| A19 | I | H | H | 8 | | 140–5 |
| A20 | III | Me | H | 8 | diastereomers | 125–145 |
| A21 | III | Me | H | 8 | | 132–150 |
| A22 | I | H | H | 10 | | see app. 5 |
| A23 | II | Me | H | 8 | diastereomers | 140–3 |
| A24 | II | Me | H | 8 | | 145–8 |
| A25 | II | Et | H | 8 | diastereomers | 145–8 |
| A26 | II | Et | H | 8 | | 155–8 |
| A27 | II | nBut | H | 8 | | 122–5 |
| A28 | II | iBut | H | 8 | | 122–5 |
| A29 | II | H | H | 10 | | see app. 6 |
| A30 | VI | H | H | 8 | | 221–3 |
| A31 | X | H | H | 8 | | 208–210 |
| A32 | VIII | H | H | 8 | | 145–165 |
| A33 | III | nPr | H | 8 | | 110–130 |

EXAMPLE 2

Step iii (Scheme B.1):

0.20 g (0.67 mmol) of triphosgene was dissolved in 10 ml of dry dichloromethane. To the latter mixture a solution of 0.70 g (2.0 mmol) of the pyrazolidine derivative and 0.42 ml (2.4 mmol) di-isopropylethylamine was added in a period of 45 minutes. The reactionmixture was stirred continuously. Subsequently, a solution containing 0.33 g (2.0 mmol) of methyl-2-adamantyl amine and 0.42 ml (2.4 mmol) of di-isopropylethylamine in 5 ml of dry dichoromethane, was added to the reactionmixture in 5 minutes. The reaction mixture was allowed to react for one night after which the solvent was evaporated in vacuo. The residu was taken into ethylacetate and the latter solution treated with 5% aqueous NaHCO$_3$ and brine respectively. The organic layer was separated and dried on MgSO$_4$. Filtration of the drying agent and removal of the solvent in vacuo yielded an oil which was subjected to flash column chromatography (SiO$_2$, eluent: CH$_2$Cl$_2$/MeOH 99/1). Collection of the product containing fractions and subsequent removal of the eluent in vacuo gave an oil which crystallized upon stirring in di-isopropylether. Filtration and drying in the air gave 0.69 g (64%) of solid B2 (m.p.: 184–6° C.).

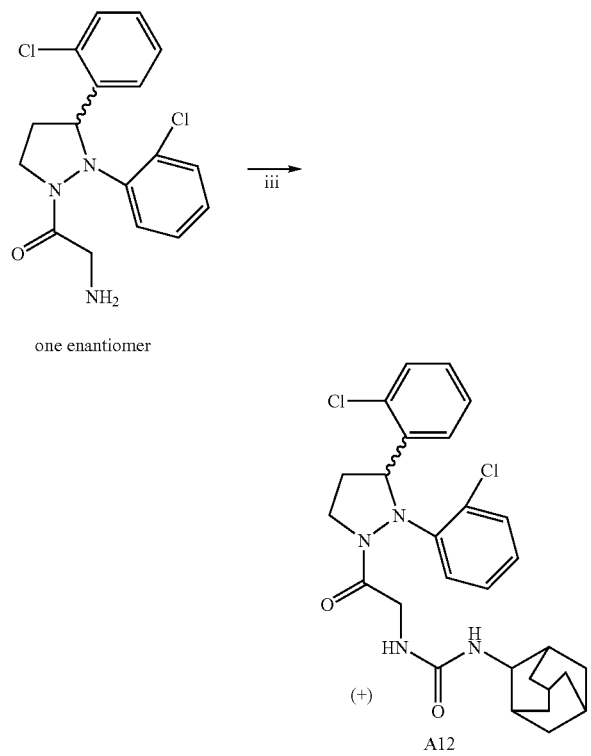

Scheme A.2

Note: The applied methyl-2-adamantyl amine can easily be prepared by standard reductive amination procedures starting from 2-adamantanon and methylamine hydrochloride while using $NaBH(OAc)_3$ as the reductive agent.

The compounds of Table B have been prepared in the same manner:

TABLE B $R_3, R_4, R_5, R_{5'}, S_2, S_4 = H$

| Compound | pyrazolidine | X | Y | $R_6$ | $R_7$ | $YR_7A$ | melting point |
|---|---|---|---|---|---|---|---|
| B1 | III | N | N | H | nPr | 11 | 132–4 |
| B2 | III | N | N | H | Me | 12 | 184–6 |
| B3 | III | N | N | Me | H | 4 | 222–4 |
| B4 | III | N | N | H | Me | 13 | 140–2 |
| B5 | III | N | O | H |  | 14 | 110–2 |
| B6 | II | N | O | H |  | 15 | 142–4 |
| B7 | II | N | O | H |  | 14 | 135–8 |
| B8 | I | N | O | H |  | 14 | 141–3 |
| B9 | I | N | O | H |  | 15 | 151–4 |

Note:
The needed intermediate after step ii (scheme B.1) in th case of B3 ($R_6$ = Me), can be prepared analogously to steps i en ii in scheme A.1.

EXAMPLE 3

Step i (Scheme C.1):

16 g (160 mmol) of succinic anhydride were dissolved in dry diethyl ether. Subsequently, 44 g (160 mmol) of II, dissolved in diethyl ether were added dropwise to the stirred succinic anhydride solution. After the addition was complete, the reaction mixture was brought to reflux temperature which was continued for one night. A precipitate had formed which was filtered, the residu was washed two times with diethyl ether. Drying on the air afforded 45.6 g (75%) of the desired intermediate.

Step ii (Scheme C.1):

Under a nitrogen atmosphere, 4.5 g (12 mmol) of the intermediate of step i and 7.9 g (61 mmol, 5.1 eq.) of diisopropylethylamine were dissolved in 50 ml of dry $CH_2Cl_2$, the resulting stirred solution was brought to 4° C. Subsequently, 0.90 g (7.0 mmol) of 1-hydroxy-7-aza-benztriazole, and 4.20 g (15 mmol) of 2-chloro-1,3-dimethylimidazolinium hexafluorophosphate were added. Then 2.19 g (15 mmol) of 2-amino-adamantane was added to the reaction mixture which was allowed to react for one hour at room temperature.

To the reaction mixture about 4 g of silica was added and concentrated in vacuo. The resulting powder was put on top of a dry column ($SiO_2$) after which elution was performed (eluent: EtOAc/petroleum ether 1/1). The part of the column containing the product was collected, and taken into MeOH. The resulting suspension was filtered, the residue washed with MeOH one time. The MeOH fractions were combined and concentrated in vacuo after which the residue was taken into $CH_2Cl_2$ and the resulting solution was dried on $MgSO_4$. After removal of the drying agent and the solvent in vacuo, a solid was obtained: 2.0 g of C2 (32%), melting point 192–5° C.

Step iii (Scheme C.1):

While stirring and under a nitrogen atmosphere, 6.0 g (60 mmol) of succinic anhydride was suspended in 35 ml of toluene. Subsequently, 2.07 g (18 mmol) N-hydroxy-succinimide, 0.73 g (6 mmol) of 4-dimethylaminopyridine, 13.3 g (18 mmol) of dry tert. butanol and 1.82 g (18 mmol) of triethylamine were added. The reaction mixture was brought to reflux temperature and allowed to react for one night. The reaction mixture was cooled, after which EtOAc was added. The resulting solution was treated respectively with 10% citric acid (aq) and brine, after which the organic fraction was dried on $MgSO_4$. Removal of the drying agent and solvent by evaporation in vacuo yielded a brown oil. Crystallization from diethylether/hexane gave 4.4 g (42%) of the desired monoester.

Step iv (Scheme C.1):

This reaction was carried out according to the procedure described in *Synthesis* (2000) p1369–71. The mono tert.butyl ester of succinic acid was methylated in the 2-position by reaction with lithium diisopropyl amide and methyliodide in tetrahydrofuran at −78° C. The isolated yield of the 2-methyl-succinic acid mono tert.butyl ester amounted to 60%.

Step v (Scheme C.1):

While stirring, 1.8 g (9.8 mmol) of 2-methyl-succinic acid mono tert.butyl ester (step iv) was dissolved in 45 ml of dry $CH_2Cl_2$ after which the solution was brought to 4° C. To the latter solution, 0.9 g (6.4 mmol) of 1-hydroxy-7-aza-benztriazole, and 4.0 g (15 mmol) of 2-chloro-1,3-dimethylimidazolinium hexafluorophosphate were added. Subsequent addition of III 4.1 g (14 mmol) did not give a raise in temperature, the reaction was allowed to proceed for a night at room temperature. Ca. 3 g of silicagel (SiO2) were added to the reaction mixture after which it was concentrated in vacuo. The resulting powder was put on top of a dry column ($SiO_2$) after which elution was performed (eluent: EtOAc/petroleum ether 1/4). The part of the column containing the product was collected and taken into MeOH. The latter suspension was filtered, the residu washed one more time with MeOH. The combined MeOH fractions were concentrated in vacuo and the resulting residue taken into $CH_2Cl_2$ after which it was dried on $MgSO_4$. Removal of the drying agent by filtration and solvent by evaporation in vacuo, 3 g (66%) of the desired intermediate was isolated.

Step vi (Scheme C.1):

Hydrolysis of the tert. butyl ester of the intermediate of step v was accomplished as follows; 3 g (6.4 mmol) of the tert. butyl ester was dissolved in 30 ml of dry $CH_2Cl_2$ after which 10 ml of trifluoroacetic acid was added dropwise. After two hours the reaction was complete, the reaction mixture was concentrated in vacuo after which the residu dissolved in a little diethylether, was put on top of a short column (dry $SiO_2$) and eluted with diethylether. The product containing eluate was concentrated in vacuo, the residue was stirred for a night in petroleum ether. Crystals were collected by filtration, after drying on the air 2.1 g (80%) were obtained of the desired intermediate.

Step vii (Scheme C.1):

Under a nitrogen atmosphere, 2.17 g (5.3 mmol) of the intermediate of step vi and 4.7 ml (27 mmol, 5.1 eq.) of diisopropylethylamine were dissolved in 25 ml of dry $CH_2Cl_2$, the resulting stirred solution was brought to 4° C. Subsequently, 0.42 g (3.1 mmol) of 1-hydroxy-7-aza-benztriazole, and 1.85 g (6.6 mmol) of 2-chloro-1,3-dimethylimi dazolinium hexafluorophosphate were added. Then 1.0 g (6.6 mmol) of 2-amino-adamantane was added to the reaction mixture which was allowed to react for one hour at room temperature.

To the reaction mixture about 4 g of silica was added and concentrated in vacuo. The resulting powder was put on top of a dry column ($SiO_2$) after which elution was performed (eluent: EtOAc/petroleum ether 1/2). The parts of the column containing the diastereomic racemates were collected separately, and taken into MeOH. The resulting two suspensions were separately filtered, each of the the two residues washed with MeOH one time. For each diastereomic racemate the corresponding MeOH fractions were combined and concentrated in vacuo after which each residue was taken into $CH_2Cl_2$ after which the two solutions were dried on $MgSO_4$. After removal of the drying agent and the solvent in vacuo, two solids, each containing one of the possible diastereomeric racemates, were obtained: 1.08 g of C8 (37%), the active racemate, melting point 238–40° C., and 1.09 g (37%) of the other, pharmacologically inactive racemate (37%) melting point 125–30° C. (not in table C).

The compounds of Table C have been obtained in a similar manner:

TABLE C $R_3, R_4, R_5, R_5', S_2, S_4 = H$
$X = C, Y = N$

| Compound | pyrazolidine | $R_6$ | $R_7$ | $YR_7A$ | melting point |
|---|---|---|---|---|---|
| C1 | III | H | H | 8 | 210–2 |
| C2 | II | H | H | 8 | 90–4 |
| C3 | II | H | H | 7 | 230–2 |
| C4 | I | H | H | 8 | 160–4 |
| C5 | I | H | H | 7 | 198–202 |
| C6 | VII | H | H | 7 | 208–210 |
| C7 | VII | H | H | 8 | 215–7 |
| C8 | III | Me | H | 8 | 238–240 |
| C9 | IX | H | H | 8 | 147–150 |

EXAMPLE 4

Step iii (Scheme D.1):

Under a nitrogen atmosphere, 0.92 g (4.9 mmol) of the intermediate of step ii and 4.4 ml (25 mmol, 5.1 eq.) of diisopropylethylamine were dissolved in 15 ml of dry $CH_2Cl_2$, the resulting stirred solution was brought to 4° C. Subsequently, 0.45 g (3.3 mmol) of 1-hydroxy-7-aza-benztriazole, and 2.1 g (7.5 mmol) of 2-chloro-1,3-dimethylimidazolinium hexafluorophosphate were added. Then 1.08 g (7.2 mmol) of 2-amino-adamantane was added to the reaction mixture which was allowed to react for one hour at room temperature. This reaction mixture was used for the following step iv.

Step iv (Scheme D.1):

To the stirred reaction mixture of step iii, 45 ml of dry $CH_2Cl_2$ were added, and 11 ml (143 mmol) of trifluoroacetic acid as well. Stirring was continued for 24 hours. The reaction mixture was concentrated in vacuo after which the residu was dissolved in a little diethylether, was put on top of a short column (dry $SiO_2$) and eluted with diethylether. The product containing eluate was concentrated in vacuo, affording 0.87 g (67%, 2 steps) of the desired acid intermediate.

Step v (Scheme D.1):

While stirring, 0.87 g (3.28 mmol) of methyl-succinic acid mono amide (step iv) was dissolved in 15 ml of dry $CH_2Cl_2$ after which the solution was brought to 4° C. To the latter solution, 0.3 g (2.2 mmol) of 1-hydroxy-7-aza-benztriazole, and 1.40 g (5.0 mmol) of 2-chloro-1,3-dimethylimidazolinium hexafluorophosphate were added. Subsequent addition of II 1.33 g (4.80 mmol) did not give a raise in temperature, the reaction was allowed to proceed for a night at room temperature. Ca. 3 g of silicagel ($SiO_2$) were added to the reaction mixture after which it was concentrated in vacuo. The resulting powder was put on top of a dry column ($SiO_2$) after which elution was performed (eluent: EtOAc/petroleum ether 1/1).

The parts of the column containing the diastereomeric racemates were collected separately, and taken into MeOH. The resulting two suspensions were separately filtered, each of the the two residues washed with MeOH one time. For each diastereomeric racemate the corresponding MeOH fractions were combined and concentrated in vacuo after which each residue was taken into $CH_2Cl_2$ after which the two solutions were dried on $MgSO_4$. After removal of the drying agent and the solvent in vacuo, two solids, each containing one of the possible diastereomeric racemates, were obtained: 0.31 g (18%) of the inactive racemate (not in table D), melting behavior: melting 90–5° C., solidifies at 130° C., remelting 160–5° C., and 0.40 g (23%) of the active racemate D1, melting behavior: melting 80–2° C., solidifies at 100° C., remelting at 125–8° C.

The compounds indicated in Table D have been prepared in a similar manner:

TABLE D $R_3, R_4, R_5', S_2, S_4 = H$
$X = C, Y = N$

| Compound | pyrazolidine | $R_5$ | $R_6$ | $YR_7A$ | remark | melting point |
|---|---|---|---|---|---|---|
| D1 | II | Me | H | 8 | | 80–2/125–8 |
| D2 | II | nBut | H | 8 | diastereomers | 80–1/150–5 |
| D3 | II | nBut | H | 8 | | 210–2 |
| D4 | II | iBut | H | 8 | | 155–8 |
| D5 | II | Et | H | 8 | diastereomers | 90–2/125–8 |
| D6 | II | Et | H | 8 | | 90–2/155–7 |

EXAMPLE 5

The 2,3-diaryl-pyrazolidines I to X used as starting materials in the above Examples 1 to 4 have been prepared as follows:

Step i (Scheme 1):

A mixture of 16.9 ml of acetic acid and 2.3 ml of water was cooled (ice/water) after which 6.8 ml of concentrated sulfuric acid was carefully added. To the cooled solution, while vigorously stirring and under a nitrogen atmosphere, 13.3 g (82 mmol) of 2-fluorophenyl hydrazine was added in portions. To the latter solution, a mixture consisting of 10.0 g (82 mmol) of 2-fluorostyrene and 2.46 g (82 mmol) of paraformaldehyde, was added portionwise while keeping the temperature below 25° C. The reaction may accumulate for some time. Vigorously stirring was continued for one night at room temperature. While cooling, 50 ml of water were added, after which extraction took place with diethyl ether (2×). The remaining aqueous fraction was made basic with 50% NaOH (aq) and subsequently extracted with diethyl ether (2×). The latter ethereal fraction was washed with water (3×) and brine (1×), and eventually dried on $MgSO_4$. Filtration of the drying agent and removal of the solvent in vacuo, yielded 16 g (75%) of a crude siruppy oil. The oil was not purified and should be stored under a nitrogen atmosphere at −20° C. to prevent oxidation of the pyrrolidine nucleus.

What is claimed is:

1. A compound of the formula (1)

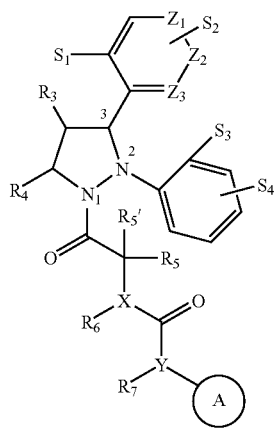

wherein, $S_1$ is chosen from hydrogen, halogen, hydroxy and alkoxy (1–3C);

$S_2$ is chosen from hydrogen and halogen;

$S_3$ is chosen from hydrogen, halogen, hydroxy and alkoxy (1–3C);

$S_4$ is chosen from hydrogen, halogen and alkyl (1–6C) optionally substituted with hydroxy, alkoxy (1–3C), amino, mono- or dialkylamino having 1–3C-atoms in the alkyl group(s), SH or S-alkyl (1–3C);

X is chosen from nitrogen and carbon;

Y is chosen from nitrogen and oxygen when X is nitrogen, or Y is nitrogen when X is carbon;

$R_3$ and $R_4$, which may be identical or different, are chosen from hydrogen and alkyl (1–3C);

$R_5$ is chosen from hydrogen and alkyl (1–6C) which may be substituted with halogen, CN, $CF_3$, hydroxy, alkoxy (1–3C), sulfonylalkyl (1–3C), amino, mono- or dialkylamino having 1–3C-atoms in the alkyl group(s) when X is carbon or nitrogen, or $R_5$ represents alkoxy (1–6C), SH or S-alkyl (1–3C) when X is carbon;

$R'_5$ is chosen from hydrogen and alkyl (1–3C);

$R_6$ is chosen from hydrogen, and alkyl (1–3C);

$R_7$ is chosen from hydrogen and alkyl (1–3C); or $R_5$ and $R_6$ together or $R'_5$ and $R_6$ together can form a 3–7 membered cyclic group which is optionally substituted with a group chosen from lower alkyl, halogen, CN and $CF_3$, and $R_5+R'_5$ together optionally form a 3–7 membered ring;

$Z_1$, $Z_2$ and $Z_3$ are chosen from carbon, or $Z_1$ is nitrogen and $Z_2$ and $Z_3$ are carbon, or $Z_1$ and $Z_3$ are carbon and $Z_2$ is nitrogen, or $Z_1$ and $Z_2$ are carbon and $Z_3$ is nitrogen;

A is chosen from a (poly) cycloalkyl system comprising 4–10 membered rings which are optionally substituted with a group chosen from halogen, $CF_3$, alkyl or alkoxy (1–3C), CN, OH and SH;

and pharmacologically acceptable salts thereof.

2. A process for the preparation of a compound as claimed in claim 1, wherein the compound is prepared according to one of the following:

A)

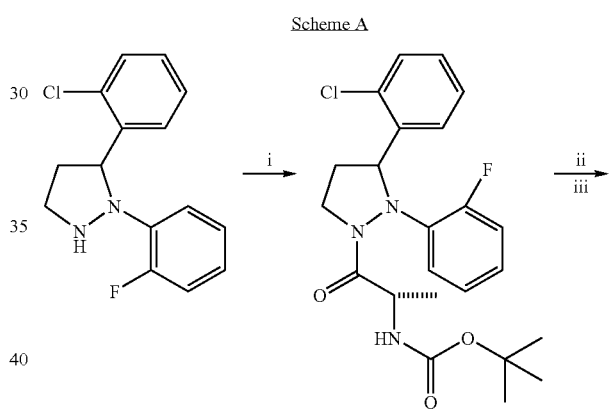

Scheme A wherein after step i two diastereomers evolve which, after step iii has been performed, can be seperated by column chromatography into enantiomeric pure diastereomers using a Chiralcel CD column (25×5 $cm^2$, 20μ, eluent; hexane/ethanol 4/1)into enantiomeric pure diastereomers;

B)
Scheme B
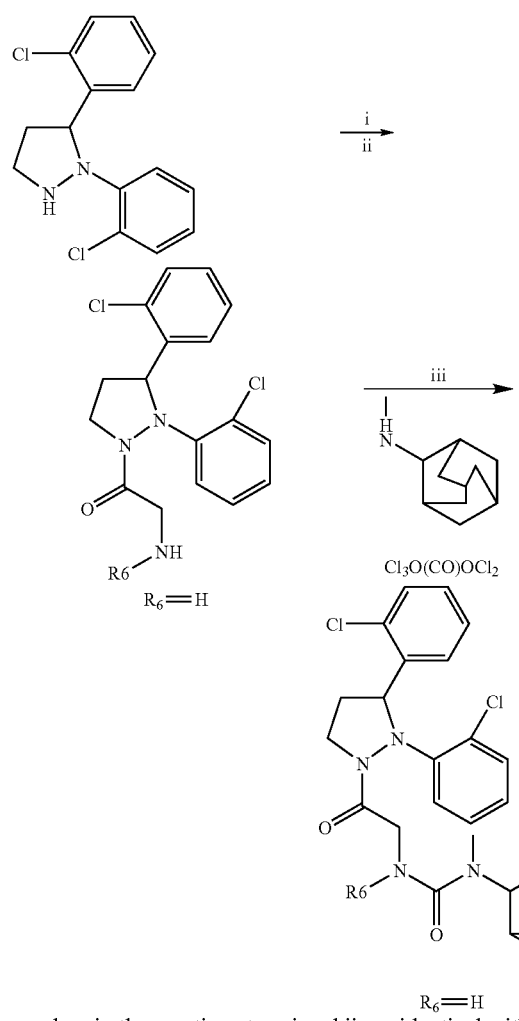
wherein the reaction steps i and ii are identical with those in scheme A;
C)
Scheme C
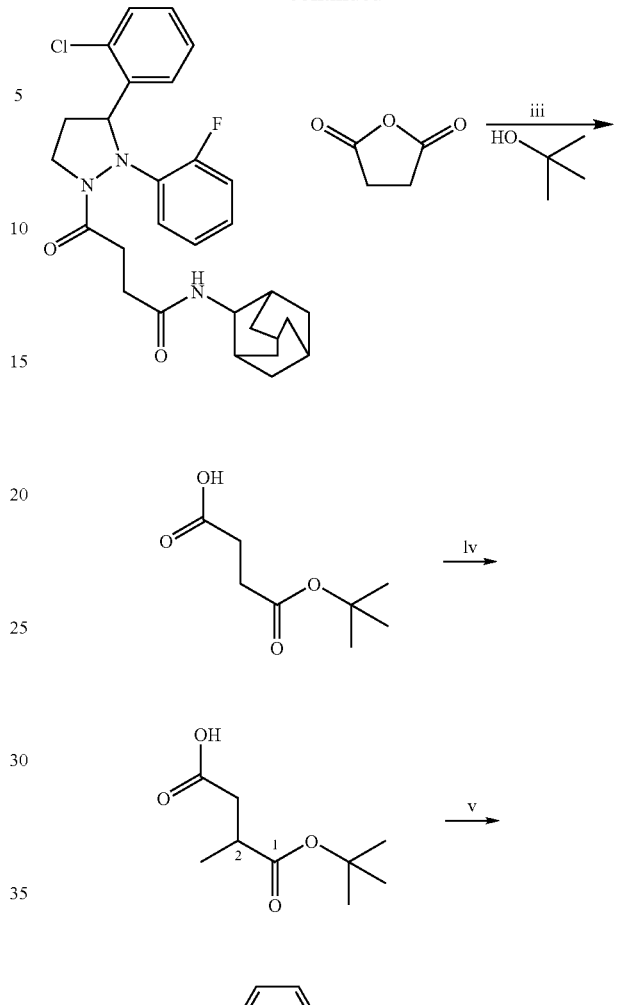
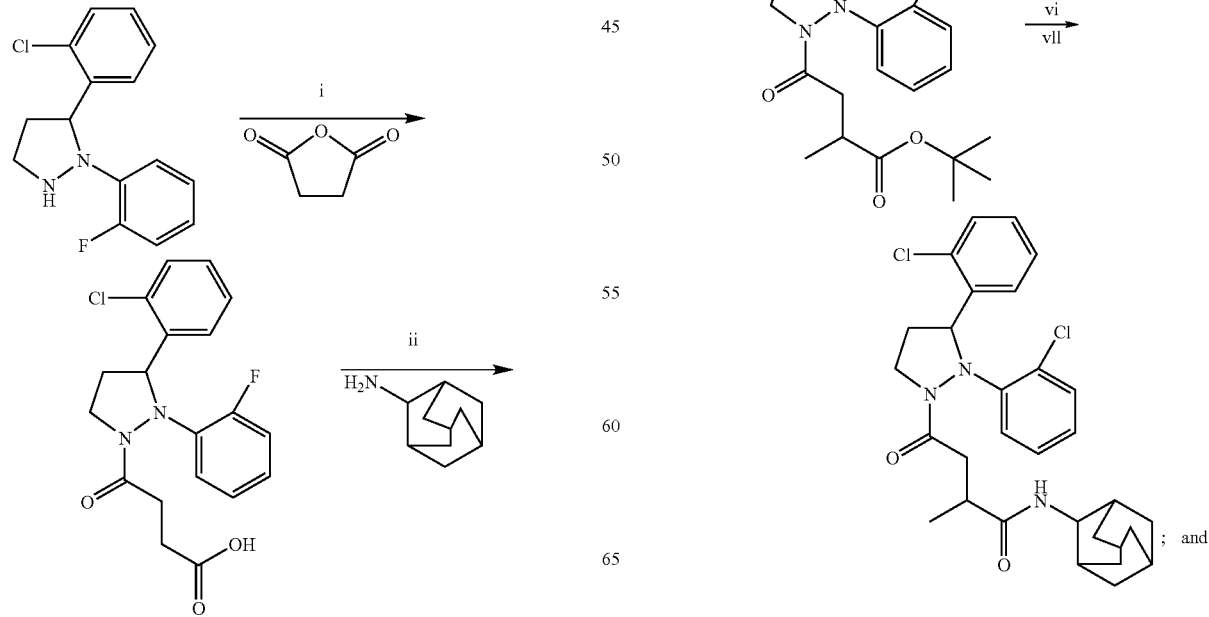

D)

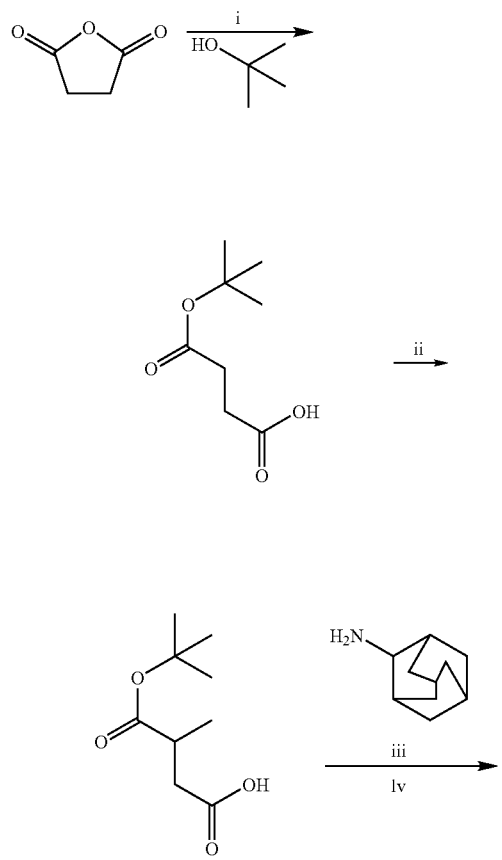

Scheme D

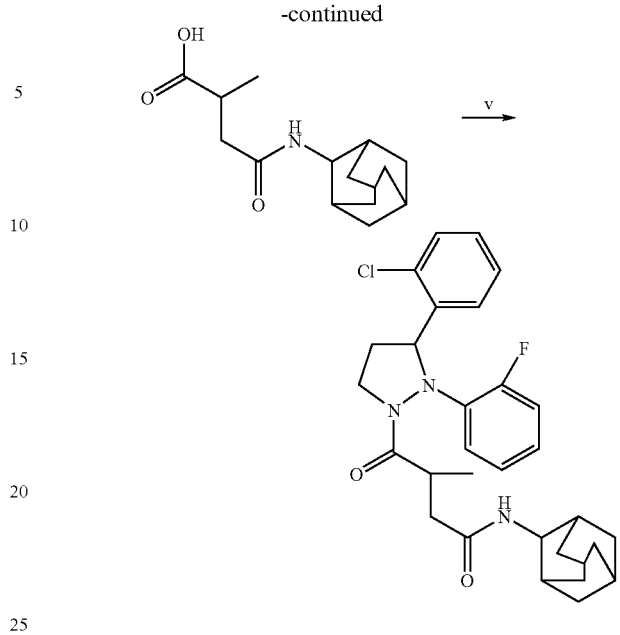

wherein the reaction steps i and ii are identical with the steps iii and iv in scheme C.

3. A pharmaceutical composition comprising at least one compound as claimed in claim 1 as an active ingredient.

4. A method of treating at least one disorder involving neurotensin mediated transmission in a patient in need thereof, comprising administering to the patient at least one compound as claimed in claim 1 in an amount effective for treating the disorder, wherein the at least one disorder is chosen from psychosis, Parkinson's disease, depression and anxiety disorders.

* * * * *

UNITED STATES PATENT AND TRADEMARK OFFICE
CERTIFICATE OF CORRECTION

PATENT NO. : 7,186,741 B2
APPLICATION NO. : 10/490549
DATED : March 6, 2007
INVENTOR(S) : Feenstra et al.

It is certified that error appears in the above-identified patent and that said Letters Patent is hereby corrected as shown below:

In claim 2, column 18, line 65, "eluent;" should read --eluent:--.

In claim 2, column 18, line 66, "4/1)into" should read --4/1 into--.

In claim 2, column 20, line 22, " lv→ " should read -- iv→ --.

In claim 2, column 20, line 45, " vi→ " should read -- vi→ --.

In claim 2, column 21, line 33, " iii→ " should read -- iii→ --.

Signed and Sealed this

Seventeenth Day of July, 2007

JON W. DUDAS
*Director of the United States Patent and Trademark Office*